United States Patent [19]

Nose

[11] 4,031,010
[45] June 21, 1977

[54] COMBINED DIALYZER AND ADSORBER UNIT

[75] Inventor: Yukihiko Nose, Cleveland Heights, Ohio

[73] Assignee: Takeda Chemical Industries, Ltd., Osaka, Japan

[22] Filed: Sept. 5, 1975

[21] Appl. No.: 610,882

Related U.S. Application Data

[63] Continuation of Ser. No. 466,513, May 2, 1974, abandoned.

[52] U.S. Cl. .............................. 210/202; 210/266; 210/317; 210/321 B; 210/494 M
[51] Int. Cl.² .................................. B01D 31/00
[58] Field of Search .......... 210/494 M, 321 K, 317, 210/266, 22, DIG. 23, 202

[56] References Cited

UNITED STATES PATENTS

| | | | |
|---|---|---|---|
| 3,357,563 | 12/1967 | Sicard | 210/266 X |
| 3,357,565 | 12/1967 | Burger | 210/494 M X |
| 3,504,796 | 4/1970 | Bray | 210/266 X |
| 3,542,199 | 11/1970 | Bray et al. | 210/317 X |
| 3,608,729 | 9/1971 | Haselden | 210/321 K |
| 3,669,878 | 6/1972 | Marantz et al. | 210/22 |
| 3,669,880 | 6/1972 | Marantz et al. | 210/22 |
| 3,884,808 | 5/1975 | Scott | 210/321 K X |

*Primary Examiner*—Frank A. Spear, Jr.
*Attorney, Agent, or Firm*—Wenderoth, Lind & Ponack

[57] ABSTRACT

A combined dialyzer and adsorber unit in one disposable package. The dialyzer is integral with the adsorber which contains a chemical adsorbent to regenerate a dialysate solution. In a preferred embodiment the dialyzer is mounted in the form of a sleeve around the adsorber container as a core. Dialysate is introduced into the dialyzer, then immediately circulated through the chemical adsorbent contained in the adsorber. There the major components of the impurities dialyzed out from the dialyzer can be adsorbed, whereby the dialysate is regenerated. The sleeve can be the adsorber and the core the dialyzer. In addition, the adsorber can have included therein, either mixed in with the adsorbent material or in a separate compartment, a water soluble dialysate material which can be dissolved by circulating water through the unit prior to starting to dialyze the patient.

11 Claims, 6 Drawing Figures

COMBINED DIALYZER AND ADSORBER UNIT

This application is a continuation of U.S. patent application Ser. No. 466,513 filed May 2, 1974, now abandoned.

The present invention relates to a combined dialyzer and adsorber unit for use in an artificial kidney system.

Currently hemodialysis is being used for treating various types of renal insufficiency and intoxication with various drugs. At this time the most commonly used dialysis approach is the use of cellulose membrane or semi-permeable membranes which allow permeation of molecules up to 36,000 molecular weight. The patient's blood is pumped into a dialyzer and while the blood is in the dialysate membrane chamber the uremic wastes, such as urea, uric acid, creatinine and other toxic substances present in the blood in excess, such as salts, can be dialyzed out through the membrane defining the chamber and picked up in dialysate passing along the other side of the membrane. By application of pressure or osmotic concentration gradients, water can be eliminated from the blood in a controlled fashion.

There are three common types of dialyzers, a parallel plate type in which parallel membranes are arranged between which the dialysate and blood flow, a capillary tube type in which a plurality of capillary tubes are provided for the blood and the dialysate flows over the capillary tubes, and a coil tube in which the blood flows through a coiled tube and the dialysate flows over the outside surfaces of the coils of the tube. It is preferred that all types be disposable after a single use to avoid the necessity of sterilization.

At the present time, for parallel plate and capillary tube type dialyzers, a single pass system of dialysate flow is used, or large dialysate tanks are used and dialysate is recirculated and at periodic intervals the entire bath is changed, or additions are made to the bath and an equal amount discarded. This last mentioned procedure is the commonly used procedure for coils.

The most commonly used dialysate flow rate is 500 cc. min. For a six-hour dialysis approximately 200 liters of dialysate is required. Even when attempts are made to reduce the dialysate flow, a 100 liter tank is still needed for most dialysate units. Thus a large amount of dialysate is presently required.

A continuous regeneration system for the dialysate can be used to reduce the amount of dialysate needed. If the dialysate can be regenerated by utilizing chemical adsorbents to adsorb the uremic wastes and toxic substances and the like from the dialysate, the artificial kidney system can be made smaller and simpler and dialysis can be made less expensive overall. Just as most dialyzers are used once and then discarded, in the regeneration system it is preferred that the chemical adsorbents also be disposable in order to simplify the process further. This requires additional disposable items such as disposable chemical adsorbent cartridges. One such separate adsorbent cartridge is presently available.

OBJECTS AND SUMMARY OF THE INVENTION

If the dialysate regeneration system and the dialyzer, both of which are disposable items, can both be accommodated in a small package, the artificial kidney system can be simpler, less expensive and easier to operate and control.

It is therefore an object of the present invention to provide a combined dialyzer and adsorber unit which is compact and which can be used in a simple artificial kidney system to permit recirculation of the dialysate and thereby reduce the size and expense of such a system.

It is a further object of the present invention to provide a combined dialyzer and adsorber unit which can be made out of easily moldable plastic material so that such a unit can be made at relatively low cost and can be discarded after a single use.

It is a still further object of the invention to provide a combined dialyzer and adsorber unit which can also be used to generate a charge of dialysate prior to starting dialysis of a patient simply by circulating pure water through the unit.

These and other objects of the invention are achieved by the combined dialyzer and adsorber unit which has a core member and a sleeve member around the core. One of the members is a dialyzer of the coiled tube type, plate type or capillary tube type, while the other member is an adsorber in the form of a mass of chemical adsorbent material in a container. The core can be the adsorber and the sleeve the dialyzer, while the sleeve can be the adsorber and the core the dialyzer. A cover is provided over one end of the unit for guiding the flow of dialysate through the unit so that it flows out of the dialyzer and into the adsorber. The parts of the unit can be made of plastic so that they are inexpensive and the unit can be discarded after a single use. The adsorber can have mixed in with the adsorbent material or in a separate compartment a water soluble dialysate material which can be dissolved in water to make a dialysate for use with the unit by circulating water through the unit prior to using the unit for dialysis.

BRIEF DESCRIPTION OF THE FIGURES

The invention will now be described in greater detail with reference to the accompanying drawings, in which.

DETAILED DESCRIPTION OF THE INENTION

Figure 1:
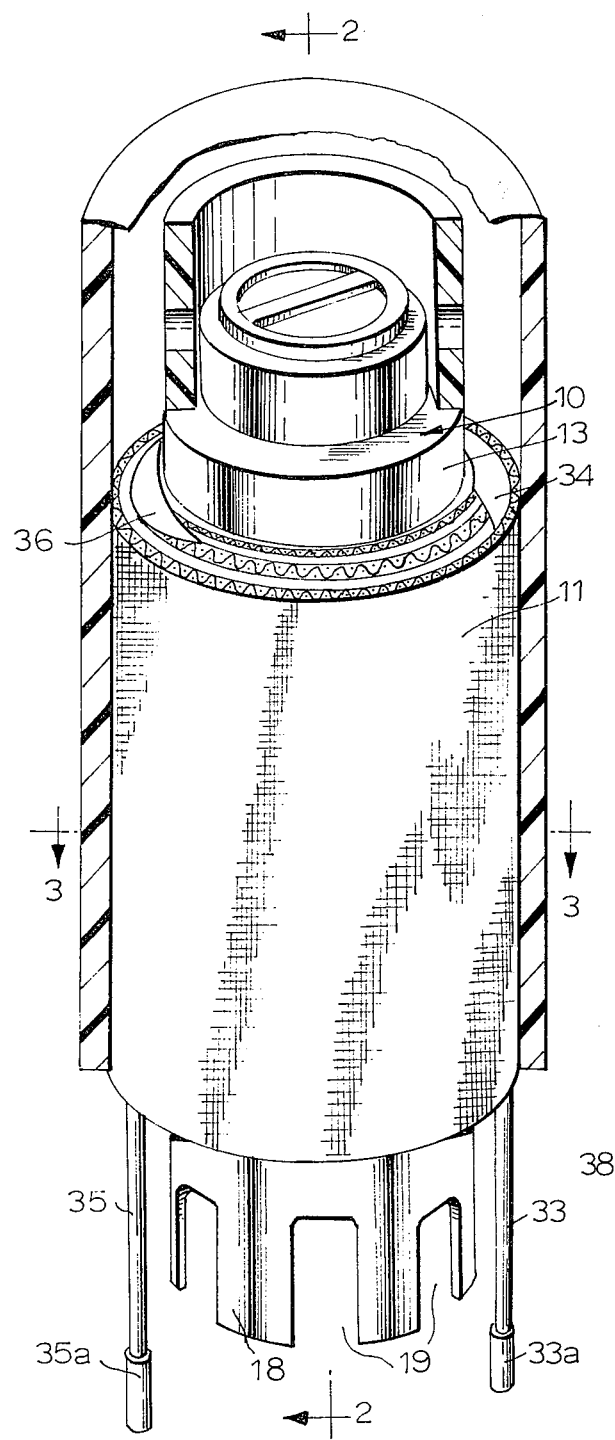
FIG. 1 is a perspective view, partly broken away, of the combined dialyzer and adsorber unit according to the invention.
Figure 3:
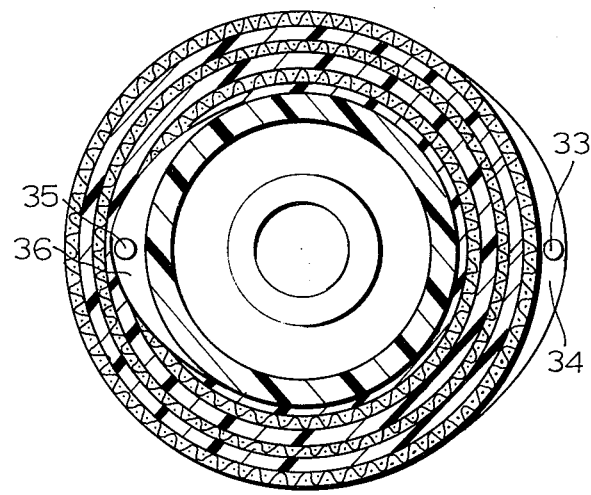
FIG. 3 is a transverse section taken on line 3—3 of FIG. 1.
Figure 2:
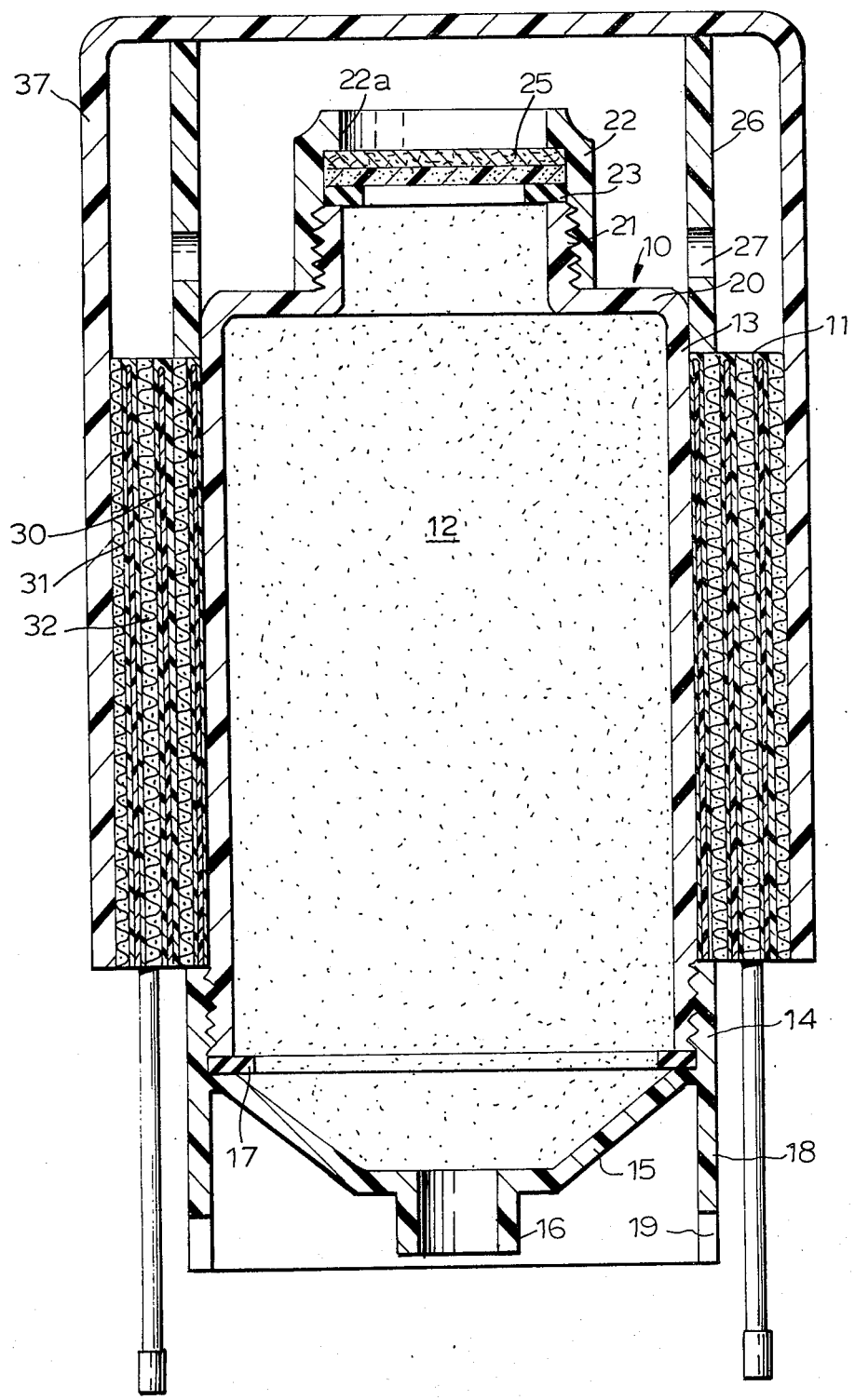
FIG. 2 is a vertical section taken on the line 2—2 of FIG. 1.

Referring first to FIGS. 1–3, the combined dialyzer and adsorber unit comprises a core generally indicated at 10 and a sleeve generally indicated at 11, and in the embodiment shown, the core 10 is constituted by an adsorbent material 12, the nature of which will be described in greater detail hereinafter, the adsorbent material being contained in a right circular cylindrical container 13. The container 13 has a bottom cover 14 threaded onto the bottom end of the container 13 and the cover has a downwardly extending conical portion 15 at the apex of which is a tubular outlet 16. Depending from the edge of the cover 14 is a depending ring 18 which has apertures 19 therein, here shown as slots extending upwardly from the bottom edge of the ring 18. At the top of the container 13 is a top end wall 20, here shown as being integral with the cylindrical portion of the container 13, and at the center of the top wall is an exteriorly threaded neck 21. A top cover 22 having an inlet aperture 22a in the top thereof is threaded onto the neck 21. Held between the bottom cover 14 and the bottom end of the cylindrical portion of the container 13 is a porous bottom retainer plate 17, and held between the top cover 22 and the top of the neck 21 is a gasket 23, and two porous top retainer plates 24 and 25. The porous retainer plates can of course also function as filters for filtering at least some of the solid material from the liquid passing through them.

A spacer means in the form of a top ring 26 is force fitted over the outside of container 13 at the top thereof and projects above the top of the cover 22. Apertures 27 are provided in this ring 26.

The sleeve 11 in the present embodiment is constituted by a dialyzer, and more specifically by a coil tube type dialyzer generally indicated at 30. The dialyzer 30 is made up of a wide flat tube 31 of a membrane material which is permeable to molecules up to 36,000 molecular weight, the most commonly used type being a cellulose material membrane, such as cellophane, Cuprophane or cellulose acetate. Between the turns or spires of the tube 31 are layers of screen 32, which layers act to space the walls of adjacent turns of the tube from each other to permit liquid to pass over the outsides of the walls of the tube. Attached to one end of the tube 31 is a blood inlet tube 33 having a coupling 33a on the free end thereof, and the tube 33 is led downwardly along a groove in a crescent shaped holder 34 which is placed against the outer surface of the container 13 prior to the start of the coiling of the tube 31 thereon. Similarly a blood outlet tube 35 having a coupling 35a on the free end thereof is attached to the other end of the tube 31 and is led downwardly along a groove in a second crescent shaped holder 36 placed against the outside of the coiled tube 31. The blood inlet and outlet tubes 33 and 35 extend downwardly and out of the bottom of the dialyzer.

Fitted tightly over the dialyzer 30 is an enclosure means, here shown as a cover 37, which holds the coiled tube 31 in place, and which also extends upwardly over the top of the ring 26 so as to completely enclose the space above the top of the dialyzer 30 and the container 13.

Figure 4:
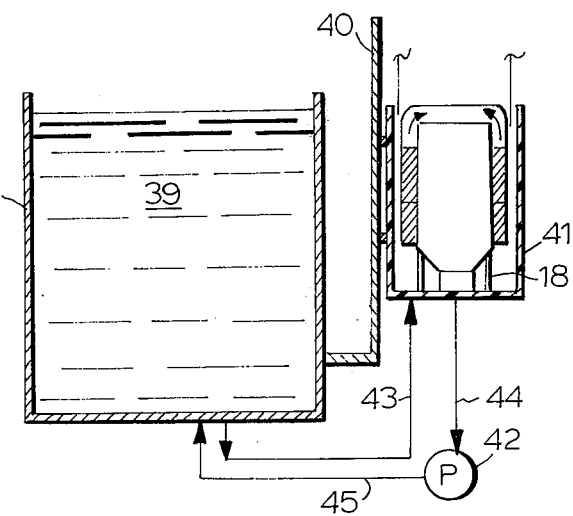
FIG. 4 is a diagram showing one way of using the combined dialyzer and adsorber unit of the invention in an artificial kidney system.

One manner in which the combined dialyzer and adsorber unit described above can be used in an artificial kidney system is shown diagrammatically in FIG. 4. A tank 38 is provided for holding the required amount of dialysate 39 to carry out a dialysis of a patient. Mounted on one wall of the tank 38 is a holder mount 40 which has secured thereto an open topped unit holder 41 in which the combined dialyzer and adsorber unit is positioned with the depending ring 18 resting on the bottom of the holder 41. The blood inlet and blood outlet tubes 33 and 35 are led upwardly along the outside of the combined dialyzer and adsorber unit out of the top of the holder 41 and attached to the patient. Extending from the bottom of the tank 38 to the bottom of the holder 41 is an intake line 43, and connected to the outlet 16 through the bottom of the holder 41 is a suction line 44 which leads to the suction side of a pump 42. From the discharge of the pump 42 a return line 45 leads back to the tank 38. Appropriate valves, (not shown) can be provided in the various lines.

In operation, dialysate 39 from the tank 38 is allowed to flow into the unit holder 41, where it will reach the same level as in the tank 38. Thereupon the pump 42 is started to create a negative pressure in the container 13. Dialysate will thus be drawn upwardly through the spaces between coils of the tube 31 which are defined by the screen layers 32, passing over the outer surfaces of the coils of the tube 31. Blood from the patient will be pumped through the interior of the tube 31 at the same time. The uremic wastes and toxic or excess substances in the blood will permeate through the wall of the tube and be picked up by the dialysate. Thus contaminated dialysate will be drawn upwardly out of the top of the dialyzer 30 and through the apertures 27 in the top ring 26 and into the interior of the container 13 through the cover inlet aperture 22a and porous retainer plates 24 and 25. The dialysate will further be drawn down through the mass of adsorbent 12 and out through the porous bottom retainer plate 17 and the outlet 16 to the pump 42 through the suction line 43. From the pump it will be pumped through the return line 45 to the tank 38.

As the contaminated dialysate is drawn through the mass of adsorbent 12, the contaminants will be adsorbed and the dialysate cleaned, so that it can be recirculated.

The particular embodiment described above is intended to be a so-called throw-away unit, and to this end the container 13 and associated parts are made of easily moldable plastic which is also inert to the dialysate, for example polyethylene. If it is desired to make the unit such that it can be reused by periodically refilling the container with adsorbent and sterilizing the unit, while a moldable plastic can be prepared which will withstand several uses, it might be preferable to use a metal such as stainless steel. As discussed above, the tube 31 can be cellulose, such as cellophane, the most commonly used membrane material. The screen layers 32 can also be plastic, for example polypropylene. The tubing is likewise preferably plastic, for example polyvinyl. The cover 37 can be any material which will fit tightly over the outside of the dialyzer. Preferably, however, the cover is a clear plastic, such as clear polyethylene, so that a visual check can be made on the dialysate flowing through the unit to make sure that no blood is leaking from the tube 31 into the dialysate.

The cover 37 has been shown as a shaped cover, for example molded. However, the expense can be reduced somewhat by making the cover 37 a flexible plastic bag or the like. The spacer means in the form of the top ring 26 becomes especially important in such a variation, since it keeps the bag from the top of the cover 22 thereby keeping the aperture 22a open for the passage of the dialysate therethrough.

The retainer plates 17, 24 and 25 can be any common filter material from which a substantially rigid plate can be made, such as molded fiberglass, or plastic, and which is inert to the dialysate.

As the chemical adsorbent, the major ingredient is activated carbon. This activated carbon has the capability of picking up organics as creatinine, uric acid, etc. Activated carbon 10–200 mesh in size, especially 16–100 mesh, is desirable. In order to prevent the mixture of microparticles into the dialysate or fragmentation of the charcoal or to keep the surface area of the charcoal large, or to prevent excessive pressure drops in the device, a granular configuration seems to be most desirable. Moreover, activated carbon paper which is prepared by incorporating activated carbon powder in a paper web in the course of making the paper is less liable to injure the semipermeable membranes and promote turbulent and eddy flows of dialysate, thereby contributing to an enhanced efficiency of dialysis. This carbon can also be made as a fiber. An additional chemical adsorbent that can be used is aluminum oxide, which is specific for the removal of inorganic phosphate. Any chemical adsorbent, particularly for a specific need, can be placed in this container. Other possibilities would be ion exchange resins, and compounds capable of removing urea as oxidized starch, and urea binders. The mixture and amount of the chemical adsorbent utilized depends upon the patient's need for certain metabolites or drugs to be removed from the blood. In addition to these passive adsorbents mentioned, an activity functioning system such as enzymes could also be used in the container.

Many variations in the structure of the present device are possible without departing from the scope of the invention. For example, the inlet aperture 22a in the top cover is shown as being in the top thereof, thereby making it necessary to insure that the cover 37 is kept clear to the top 22. By making the structure such that the openings in the upper end of the container were lateral openings the necessity for a spacer means could be eliminated. Moreover, the provision of a removal cover at the upper end of the container is not necessary as long as there is a removable cover at the bottom of the container, and vice versa. In the preferred embodiment, the dialyzer is shown and described as a coil tube dialyzer. However, a parallel plate type dialyzer or a capillary tube type dialyzer could easily be designed in the form of a sleeve which could be placed on the container 13 as the core in place of the coil tube type dialyzer 30. The blood inlet and outlet tubes 33 and 35 could extend upwardly instead of downwardly, and be sealed in cover 37. In the foregoing the sleeve 11 has been shown and described as the dialyzer and the core 10 as the absorber. Minor changes in design could easily be made to make the core the dialyzer and the sleeve the adsorber, in which case the preferred flow path would be upwardly through the dialyzer core and then downwardly through the adsorber sleeve. Such an arrangement is shown in FIG. 5.

Figure 5:
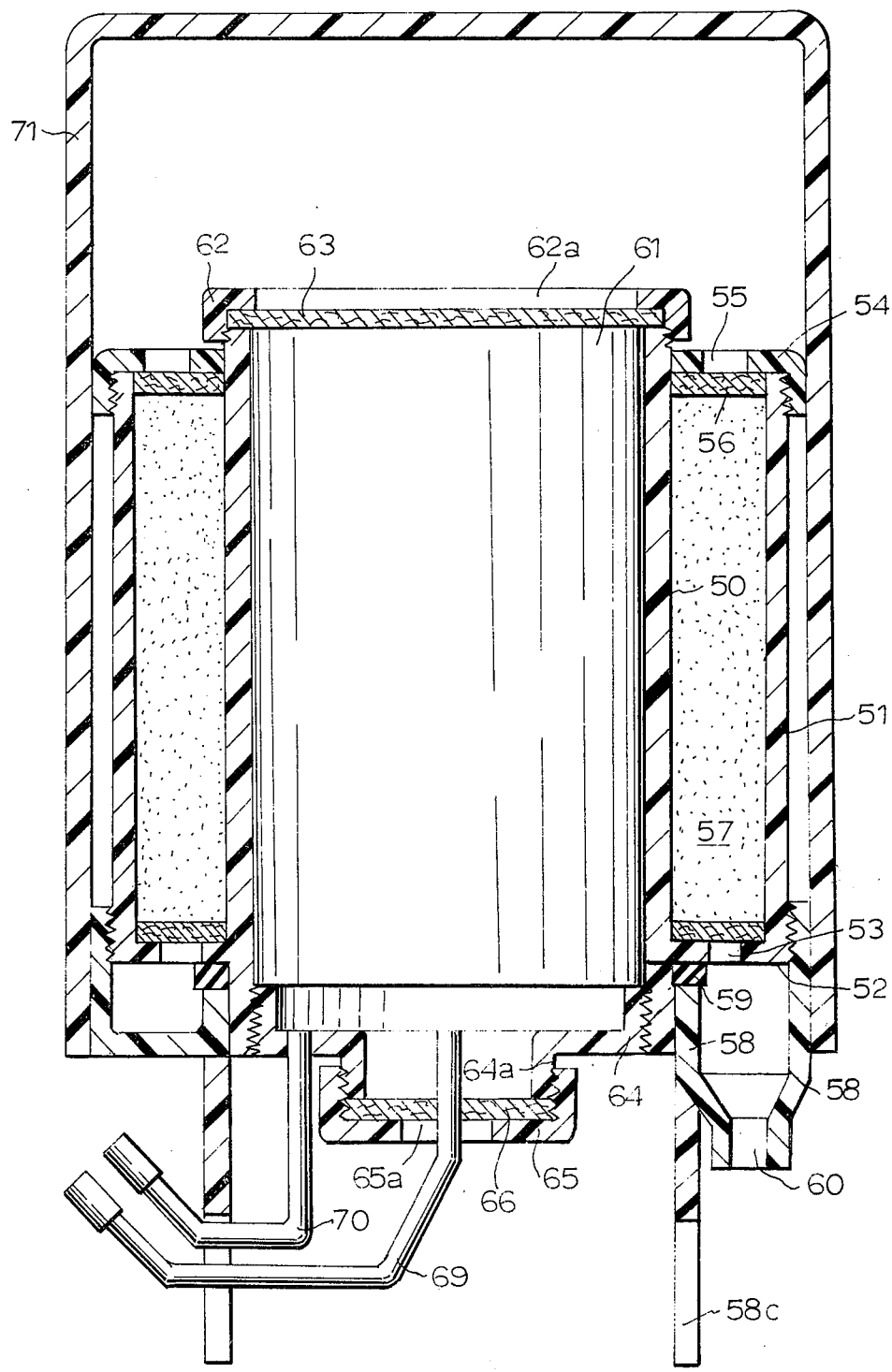
FIG. 5 is a view similar to FIG. 2 of a modified embodiment of the unit.

As seen in FIG. 5, the unit comprises a container 50 which is generally a right circular cylinder, and on the outside thereof is a bottom wall 52 from the outer edge of which extends an outer wall 51 generally concentric to the container 50. There is defined within these walls an annular sleeve which is filled with an adsorbent 57. The bottom wall has a series of apertures 53 therein, and in the bottom of the annular sleeve is a porous retainer plate 53a. This plate is held in position by the weight of the adsorbent 57. Over the top of the sleeve is an annular top cover 54 which is threaded onto the outer wall 51, and which holds an annular porous retainer plate 56 against the top of the wall 51. The top cover 54 also has a series of apertures 55 therein.

Threaded onto the lower end of the lower wall 51 is an annular bottom cover 58 having an outer wall 58a and an inner wall 58b. The top end of the outer wall is in threaded engagement with the bottom end of the outer wall 51, and the top end of the inner wall 58b presses a gasket 59 against the bottom surface of the bottom wall around the bottom of the container 50. At one point around the circumference of the bottom cover 58 is an outlet 60. Projecting downwardly at intervals around the circumference of the inner wall 58b are legs 58c.

Within the container 50 is a dialyzer 61, the details of which are not shown, which can be the same as that shown in FIGS. 1–3, i.e. having a tube with layers of screen between the turns of the coiled tube, or can be a capillary or flat tube type. Actually the latter is preferred in this embodiment. A bottom plug 64 is threaded into the lower end of the container 50, and it has a neck 64a thereon which is covered by a bottom dialyzer cover 65 threaded thereon and having a bottom dialyzer aperture 65a therein. A porous bottom dialyzer retainer plate 66 can, if desired, be provided under the cover 65, being held against the neck 64a by the cover 65. A blood inlet tube 70 extends through the plug 64 to one end of the dialyzer 61, and a blood outlet tube extends through the retainer plate 66 from the other end of the dialyzer 61. The top of the container 50 is closed by a top dialyzer cover 62 threaded onto the top end of the container 50, the top dialyzer cover having an outlet aperture 62a therein and holding a porous retainer plate 63 against the top end of the container 50. Finally a cover 71 is fitted tightly over the outside of the sleeve, the cover here being shown as a rigid cover which extends upwardly above the top of the container 50. If a flexible material cover is used, some spacer means such as the top ring 26 of FIGS. 1–3 must be used.

This embodiment of the unit can be used in the same manner as that of FIGS. 1–3, that is the suction pump is attached to the outlet 60 and dialysate is supplied to the holder in which the unit is positioned. The dialysate is drawn upwardly through the container 50 and the dialyzer 61 therein overflows through the aperture 62a in the cover 62 and is then drawn downwardly through the adsorbent 57 in the sleeve. The thus cleansed dialysate is collected in the bottom cover 58 and drawn out through the outlet 60.

If a configuration more nearly like that of FIGS. 1–3 is used, i.e. with a conical portion and neck at the bottom of the container, the pressure side of the pump can be connected to pump dialysate first through the container 50 and then through adsorbent 57.

The unit can be modified further to provide a charge of a water soluble dialysate material in an amount such that when a predetermined amount of water is circulated through the unit, the desired amount of dialysate is automatically prepared. One way to do this is in the embodiment of FIGS. 1–3 simply to mix in with the adsorbent material 12 the desired amount of soluble dialysate material, and then prior to starting the flow of blood from the patient through the dialyzer to pump pure water in an amount equal to the amount of dialysate required through the unit until the soluble dialysate material is completely dissolved. However, some dialysate materials should not be stored in contact with the adsorbent materials. An embodiment of the unit in which the dialysate material is kept separate from the adsorbent material is shown in FIG. 6.

Figure 6:
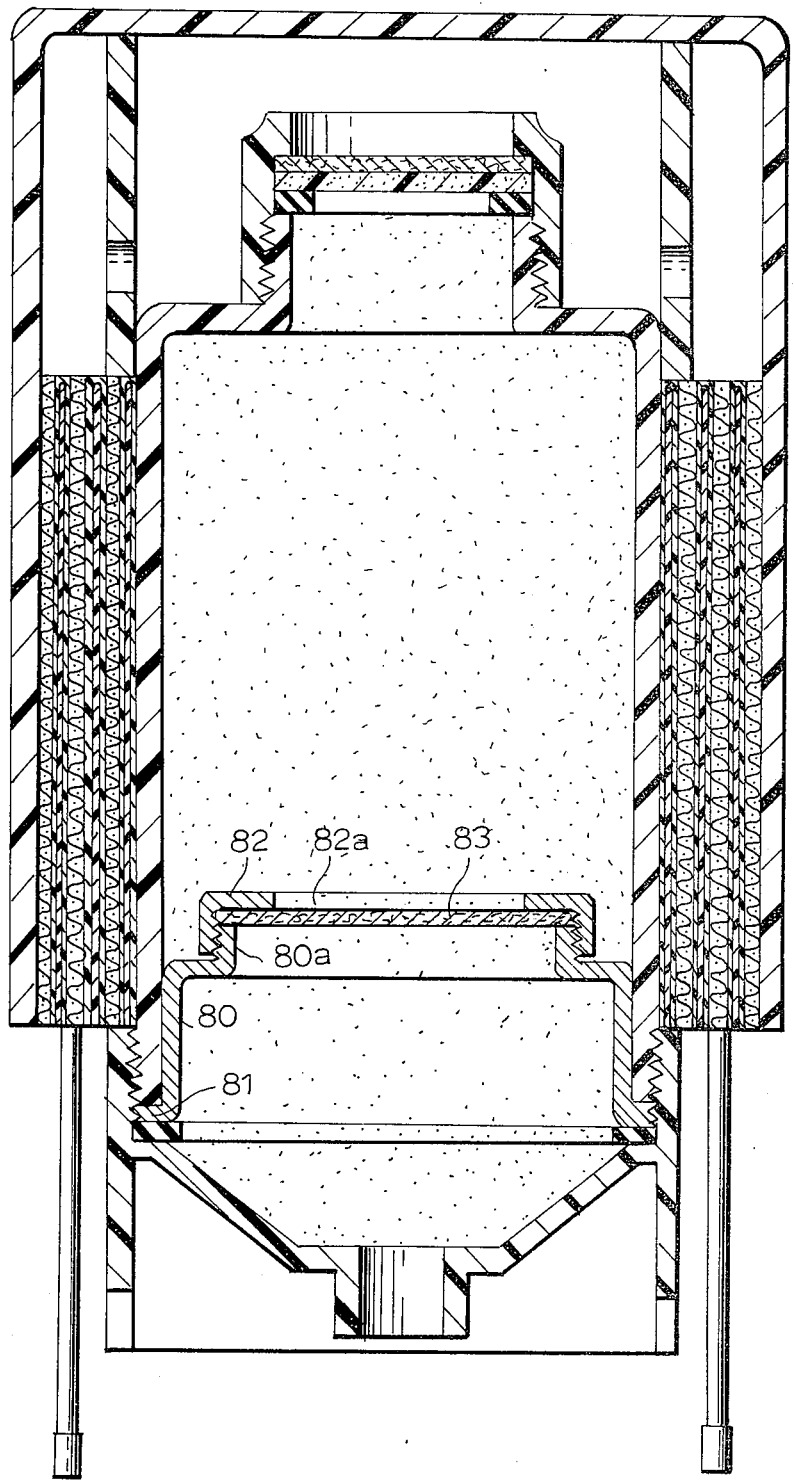
FIG. 6 is a view similar to FIG. 2 of a further modified embodiment of the unit.

In FIG. 6, the structure of the unit is essentially the same as that of FIGS. 1–3. However, there has been added to the interior of the container 10 a dialysate material cup 80. This cup has a lip 81 which is held between the retainer plate 17 and the end of the container 10. The wall of the cup extends along the inside of the wall of the container 10 and has a threaded neck 80a thereon over which is threaded a cup cover 82 having an aperture 82a therein. A porous retainer plate 83 is held between the cover 82 and the neck 80a. The anhydrous soluble dialysate material is placed in the cup, and when water is passed through the unit prior to its operation as a dialysis unit, the water dissolves the dialysate material after which the cup 80 remains empty for the rest of the time the unit is in use.

The advantages of such an arrangement are many. The provision of the proper amount of dialysate material in the unit eliminates the need to have a specially trained person prepare the dialysate for use in the unit. A relatively untrained person can install the unit in the artificial kidney system and circulate a measured amount of water through the unit before starting to dialyze the patient.

Moreover, combined dialyzer and adsorbent units can be made up ahead of time for different types of dialysis.

It will be seen that there has been provided a simple yet compact unit which is easy to use and can be used in many different types of dialysis. By recirculating dialysate through the unit, the amount of dialysate needed can be greatly reduced. The heretofore unused space in a coil tube type dialysis unit has been utilized, thereby making the overall unit more compact and portable. The unit can be used in simple apparatus such as an open tank or a tank with a separate holder for the unit. By making the device out of inexpensive materials, not only can the cost be reduced but the unit can be made as a throw-away unit, thereby avoiding the necessity for sterilizing, recharging with adsorbent, etc. and thus reducing the time and labor involved in carrying out dialysis. By providing the dialysate material in a premeasured amount in water soluble form right in the unit, not only is the need for specially trained personnel minimized, but an opportunity for mistakes in the preparation of the dialysate is eliminated.

It is thought that the invention and its advantages will be understood from the foregoing description and it is apparent that various changes may be made in the form, construction and arrangement of the parts without departing from the spirit and scope of the invention or sacrificing its material advantages, the forms hereinbefore described and illustrated in the drawings being merely preferred embodiments thereof.

What is claimed is:

1. An artificial kidney apparatus comprising, in combination, a combined dialyzer and adsorber unit having a cylindrical container having a top cover with an aperture therein and an apertured bottom cover and a mass of adsorbent therein, a flat tube of membrane material permeable to uremic wastes and toxic materials in blood wrapped in a coil around said cylindrical container, a screen layer between each of the coils of the tube, a blood inlet tube connected to one end of the flat tube and a blood outlet tube connected to the other end of the flat tube, said blood tubes extending to the exterior of the sleeve, and a unit cover over said coil around said cylindrical container and over the end of the container having the top cover thereon and being spaced from the top cover sufficiently to give access to the aperture in the cover, the bottom of said cover being completely open for exposing the entire area of the edges of said screen layers toward the bottom of said unit, said container and covers being of a moldable plastic inert to the dialysate, said aperture in said top cover being sufficiently large to receive liquid flowing simultaneously through all of said screen layers around the entire circumference of said screen layers;
a dialysate holding tank;
a unit holder tank in which said unit is positioned with said unit cover at the top thereof;
a dialysate intake line extending from said dialysate tank to unit holder tank;
a dialysate pump;
a suction line extending from said adsorber outlet to the intake of said dialysate pump; and
a return line from the outlet of said dialysate pump to said diaylsate holding tank,
whereby when dialysate fills said unit holder tank with the uncovered edges of said screen layers immersed in dialysate and dialysate is caused to flow through the unit, dialysate flows evenly over the turns of the coil along the screen layers around the entire periphery of the unit and all of the coil is utilized for exchange of impurities from the blood within the coil to the dialysate flowing over the outside of the coil.

2. A combined dialyzer and adsorber unit comprising a cylindrical container having a top cover with an aperture therein and an apertured bottom cover and a mass of adsorbent therein, a flat tube of membrane material permeable to uremic wastes and toxic materials in blood wrapped in a coil around said cylindrical container, a screen layer between each of the coils of the tube, a blood inlet tube connected to one end of the flat tube and a blood outlet tube connected to the other end of the flat tube, said blood tubes extending to the exterior of the sleeve, and a unit cover over said coil around said cylindrical container and over the end of the container having the top cover thereon and being spaced from the top cover sufficiently to give access to the aperture in the cover, the bottom of said cover being completely open for exposing the entire area of the edges of said screen layers toward the bottom of said unit, said container and covers being of a moldable plastic inert to the dialysate, said aperture in said top cover being sufficiently large to receive liquid flowing simultaneously through all of said screen layers around the entire circumference of said screen layers, whereby when said unit is placed in a body of dialysate with the uncovered edges of said screen layers immersed in dialysate and dialysate is caused to flow through the unit, dialysate flows evenly over the turns of the coil along the screen layers around the entire periphery of the unit and all of the coil is utilized for exchange of impurities from the blood within the coil to the dialysate flowing over the outside of the coil.

3. A combined dialyzer and adsorber unit as claimed in claim 2 in which said unit cover is a flexible plastic bag and said unit further comprising a spacing means on said container extending beyond said cover on the end of the container and over which said unit cover engages for keeping the unit cover spaced from the container cover.

4. A combined dialyzer and adsorber unit as claimed in claim 2 in which said spacing means is a ring of plastic having apertures therein and force fitted over the end of said container.

5. A combined dialyzer and adsorber unit as claimed in claim 2 in which said container has a plurality of legs extending from the end opposite said the end having said spacing means thereon on which said unit can be stood in a tank to permit circulation of dialysate therearound.

6. A combined dialyzer and adsorber unit comprising a cylindrical container having a top cover with an aperture threin and an apertured bottom cover and a mass of granular material therein consisting of a mixture of an adsorbent and a water soluble dialysate material, a flat tube of membrane material permeable to uremic wastes and toxic materials in blood wrapped in a coil around said cylindrical container, a screen layer between each of the coils of the tube, a blood inlet tube connected to one end of the flat tube and a blood outlet tube connected to the other end of the flat tube, said blood tubes extending to the exterior of the sleeve, and a unit cover over said coil around said cylindrical container and over the end of the container having the top cover thereon and being spaced from the top cover sufficiently to give access to the aperture in the cover, the bottom of said cover being completely open for exposing the entire area of the edges of said screen layers toward the bottom of said unit, said container and covers being of a moldable plastic inert to the dialysate, said aperture in said top cover being sufficiently large to receive liquid flowing simultaneously through all of said screen layers around the entire circumference of said screen layers, whereby when said unit is placed in a body of dialysate with the uncovered edges of said screen layers immersed in dialysate and dialysate is caused to flow through the unit, dialysate flows evenly over the turns of the coil along the screen layers around the entire periphery of the unit and all of the coil is utilized for exchange of impurities from the blood within the coil to the dialysate flowing over the outside of the coil.

7. A combined dialyzer and adsorber unit comprising a cylindrical container having a top cover with an aperture therein and an apertured bottom cover and a mass of adsorbent therein, a dialysate material cup positioned inside said container and having an aperture in the bottom thereof for permitting liquid to pass through the cup, and a water soluble dialysate material in said cup, a flat tube of membrane material permeable to uremic wastes and toxic materials in blood wrapped in a coil around said cylindrical container, a screen layer between each of the coils of the tube, a blood inlet tube connected to one end of the flat tube and a blood outlet tube connected to the other end of the flat tube, said blood tubes extending to the exterior of the sleeve, and a unit cover over said coil around said cylindrical container and over the end of the container having the top cover thereon and being spaced from the top cover sufficiently to give access to the aperture in the cover, the bottom of said cover being completely open for exposing the entire area of the edges of said screen layers toward the bottom of said unit, said container and covers being of a moldable plastic inert to the dialysate, said aperture in said top cover being sufficiently large to receive liquid flowing simultaneously through all of said screen layers around the entire circumference of said screen layers, whereby when said unit is placed in a body of dialysate with the uncovered edges of said screen layers immersed in dialysate and dialysate is caused to flow through the unit, dialysate flows evenly over the turns of the coil along the screen layers around the entire periphery of the unit and all of the coil is utilized for exchange of impurities from the blood within the coil to the dialysate flowing over the outside of the coil.

8. A combined dialyer and adsorber unit as claimed in claim 7 in which said cup is a moldable plastic material inert to the dialysate.

9. A combined dialyzer and adsorber unit comprising a cylindrical container having a top cover with an aperture therein and an apertured bottom cover for holding a mass of adsorbent therein, a flat tube of membrane material permeable to uremic wastes and toxic materials in blood wrapped in a coil around said cylindrical container, a screen layer between each of the coils of the tube, a blood inlet tube connected to one end of the flat tube and a blood outlet tube connected to the other end of the flat tube, said blood tubes extending to the exterior of the sleeve, and a unit cover over said coil around said cylindrical container and over the end of the container having the top cover thereon and being spaced from the top cover sufficiently to give access to the aperture in the cover, the bottom of said cover being completely open for exposing the entire area of the edges of said screen layers toward the bottom of said unit, said container and covers being of a moldable plastic inert to the dialysate, said aperture in said top cover being sufficiently large to receive liquid flowing simultaneously through all of said screen layers around the entire circumference of said screen layers, whereby when said unit is placed in a body of dialysate with the uncovered edges of said screen layers immersed in dialysate and dialysate is caused to flow through the unit, dialysate flows evenly over the turns of the coil along the screen layers around the entire periphery of the unit and all of the coil is utilized for exchange of impurities from the blood within the coil to the dialysate flowing over the outside of the coil.

10. A combined dialyzer and adsorber unit as claimed in claim 9 in which said container and covers are of a moldable plastic inert to the dialysate.

11. A combined dialyzer and adsorber unit as claimed in claim 9 in which said unit cover is a flexible plastic bag, and said unit further comprising a spacing means on said container extending beyond said cover on the end of the container and over which said unit cover engages for keeping the unit cover spaced from the container cover.

* * * * *